US006672036B2

(12) United States Patent
Banks

(10) Patent No.: US 6,672,036 B2
(45) Date of Patent: *Jan. 6, 2004

(54) METHOD AND PACKAGING SYSTEM FOR PACKAGING A STERILIZED ITEM

(76) Inventor: Percival C. Banks, 1301 Quarry Ct., Suite 204, Richmond, CA (US) 94801

( * ) Notice: Subject to any disclaimer, the term of this patent is extended or adjusted under 35 U.S.C. 154(b) by 82 days.

This patent is subject to a terminal disclaimer.

(21) Appl. No.: 10/100,153

(22) Filed: Mar. 18, 2002

(65) Prior Publication Data

US 2002/0092274 A1 Jul. 18, 2002

Related U.S. Application Data

(63) Continuation-in-part of application No. 09/616,100, filed on Jul. 14, 2000, now Pat. No. 6,578,348.

(51) Int. Cl.[7] .............................................. B65B 55/02
(52) U.S. Cl. .............................. 53/459; 53/425; 53/570
(58) Field of Search ........................... 53/133.1, 133.3, 53/411, 425, 459, 464, 469, 570; 206/439, 459.5; 220/495.11; 383/88, 127

(56) References Cited

U.S. PATENT DOCUMENTS

| 2,023,782 | A | * | 12/1935 | Driver | 383/123 |
| 3,107,786 | A | * | 10/1963 | Adelman | 206/278 |
| 3,217,934 | A | * | 11/1965 | Schneider et al. | 222/107 |
| 3,224,640 | A | * | 12/1965 | Schneider et al. | 222/107 |
| 3,446,420 | A | * | 5/1969 | Rinecker | 383/89 |
| 3,494,726 | A | * | 2/1970 | Barasch | 422/29 |
| 4,705,171 | A | * | 11/1987 | Eldridge | 206/438 |
| 4,852,783 | A | * | 8/1989 | Bryden et al. | 224/684 |
| 5,638,661 | A | * | 6/1997 | Banks | 53/469 |
| 6,578,348 | B1 | * | 6/2003 | Banks | 53/425 |

* cited by examiner

Primary Examiner—Scott A. Smith
Assistant Examiner—Nathaniel Chukwurah
(74) Attorney, Agent, or Firm—H. Michael Brucker

(57) ABSTRACT

A method, packaging system and packaging element for packaging a sterilizable item for aseptic presentation onto a sterile field wherein the vertical orientation of the sterilizable item does not need to be reversed during packaging, sterilization, unpackaging or presentation and instructions for handling are printed on the packaging element so that they are exposed when the packaging element is folded according to the packaging system and method.

20 Claims, 6 Drawing Sheets

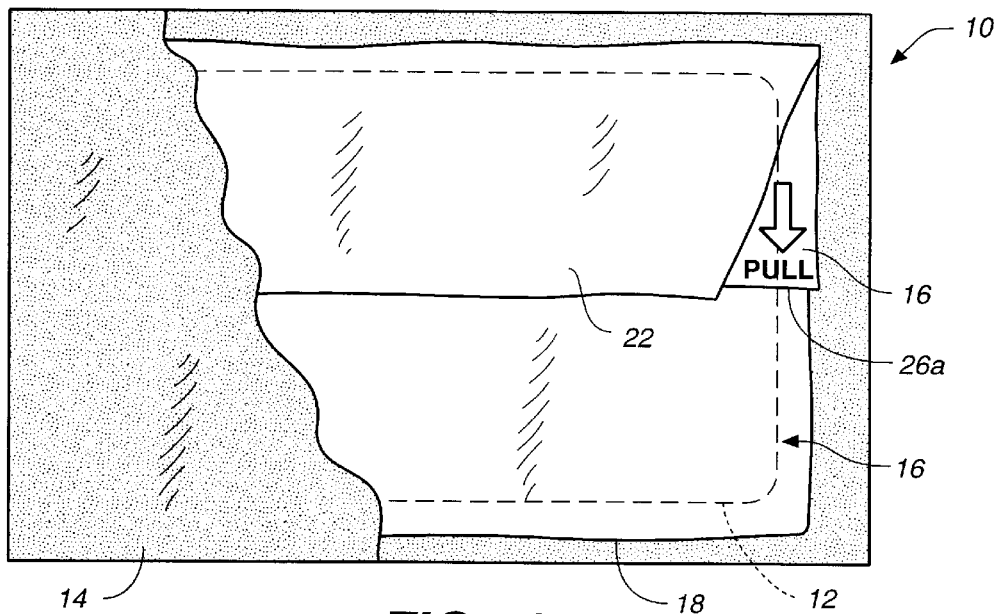
FIG._1
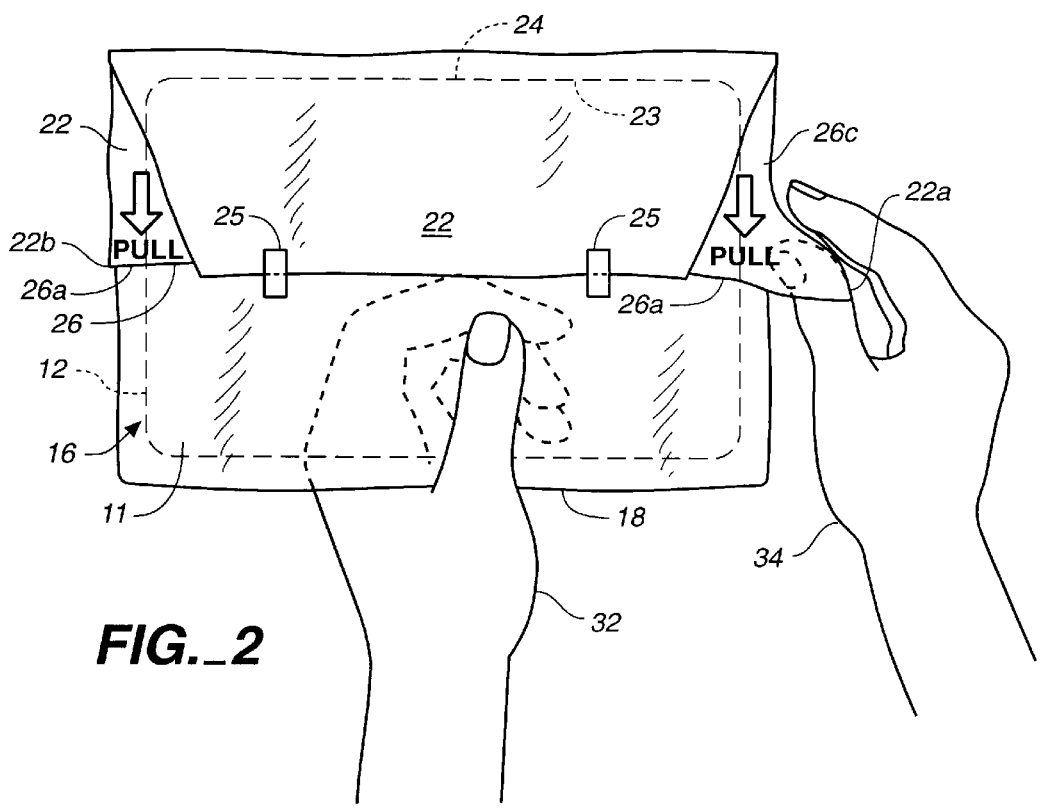
FIG._2

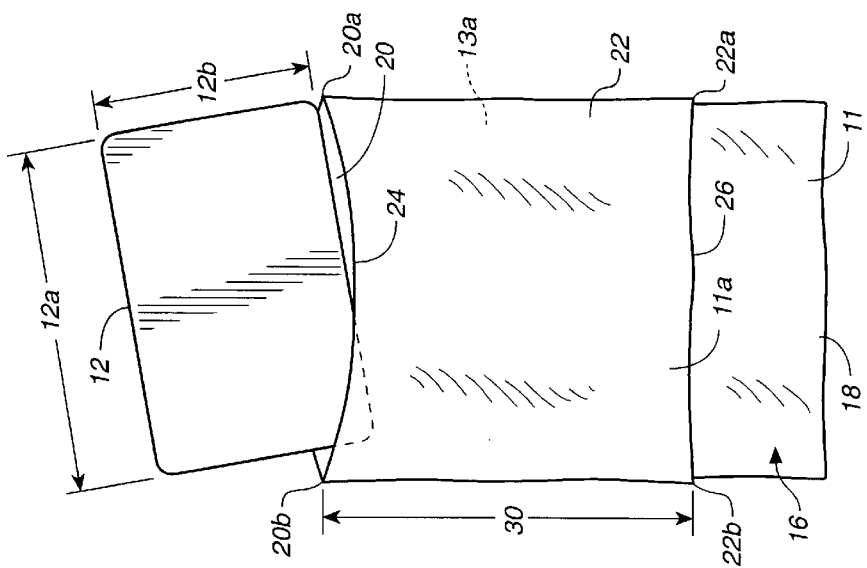
FIG._4
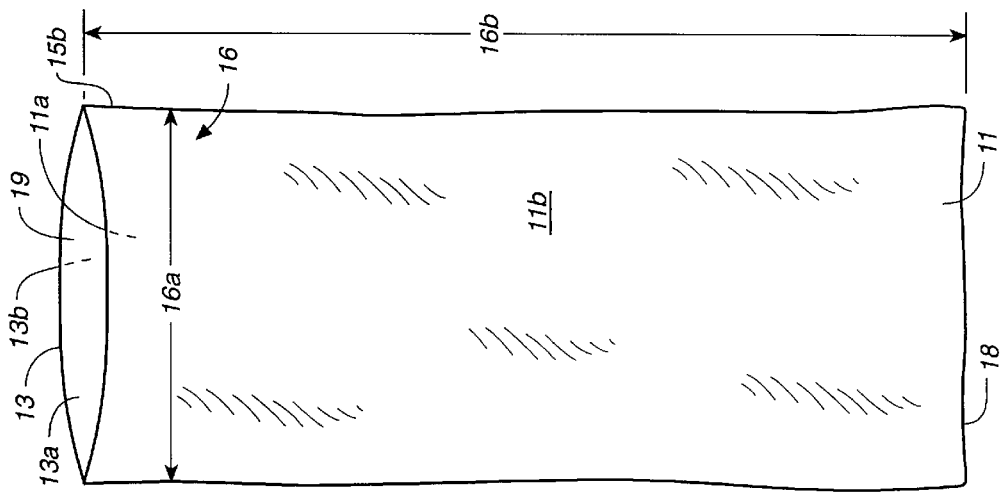
FIG._3

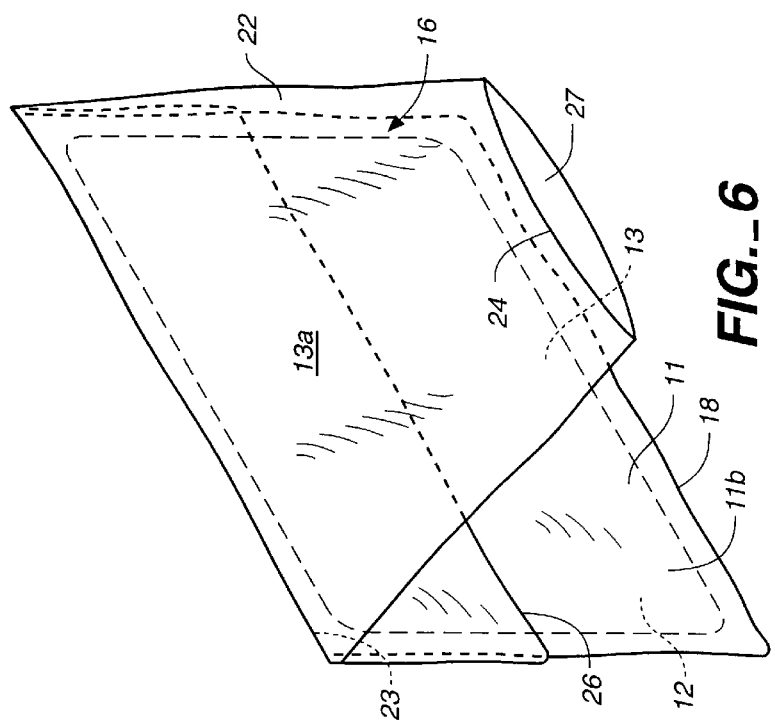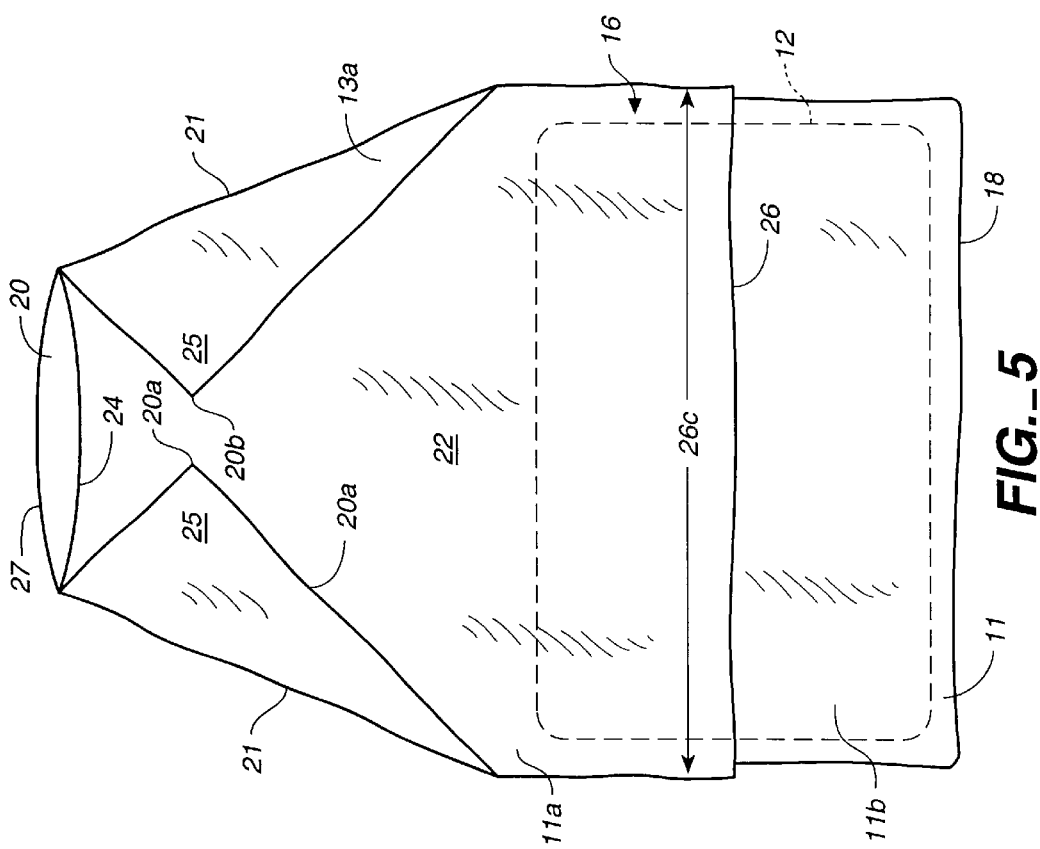

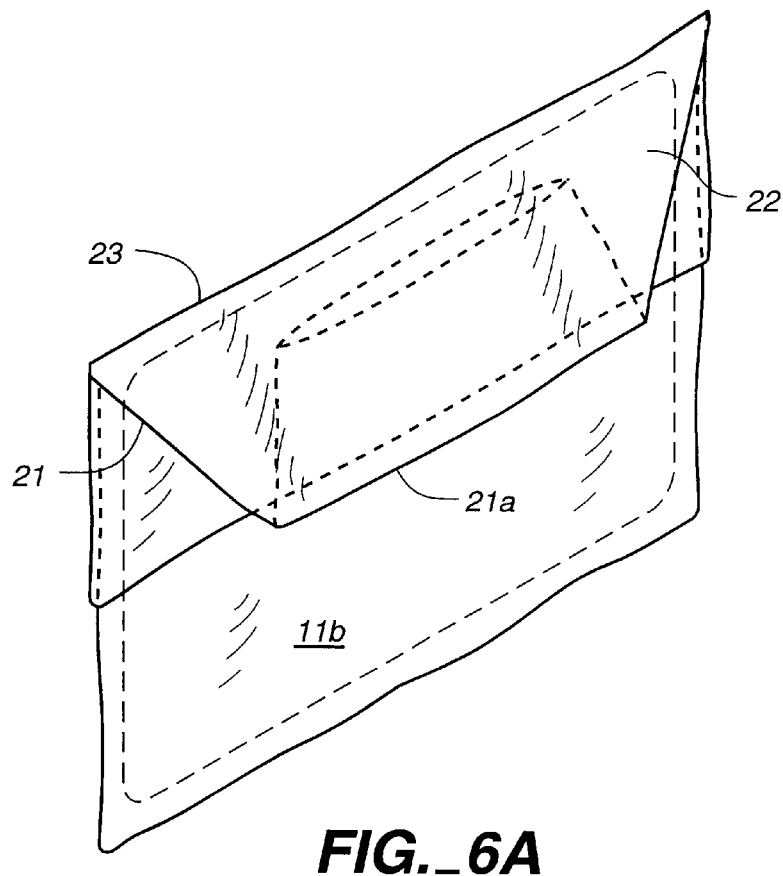
FIG._6A
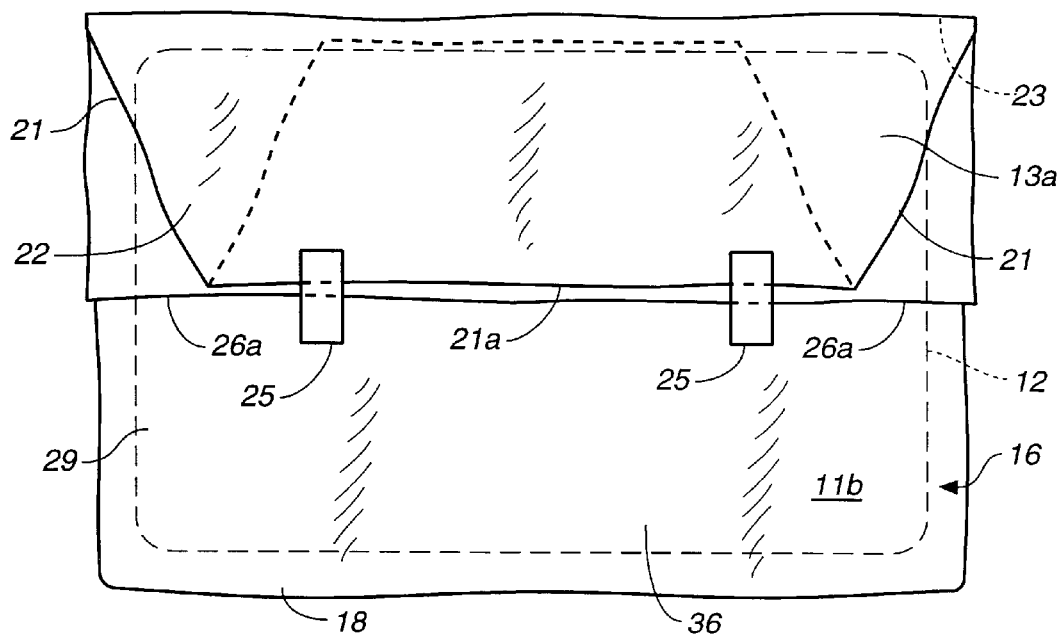
FIG._7A

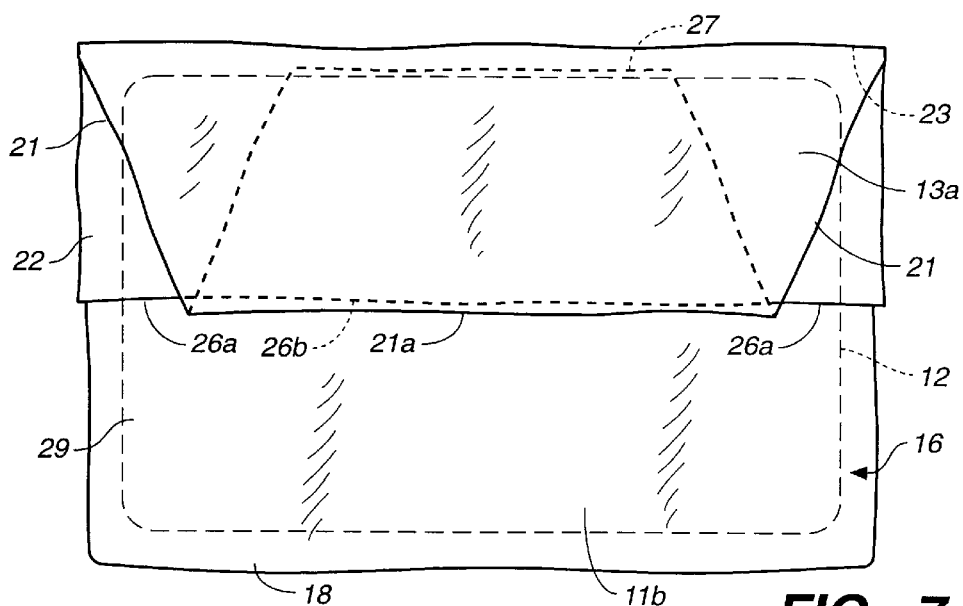
FIG._7
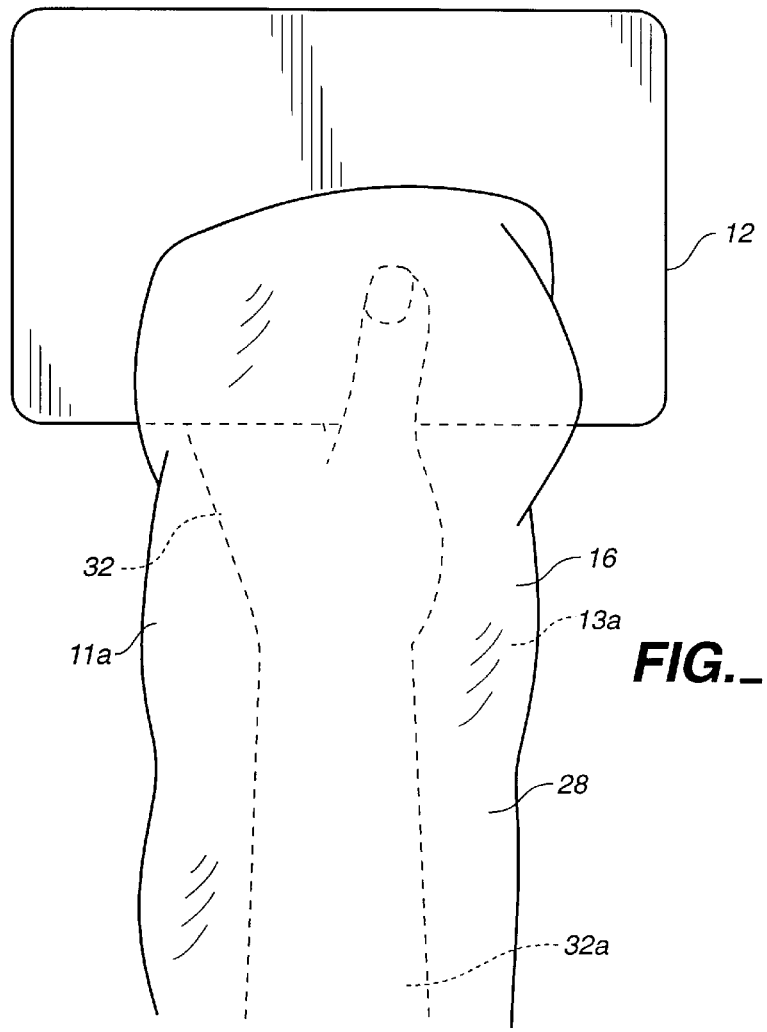
FIG._8

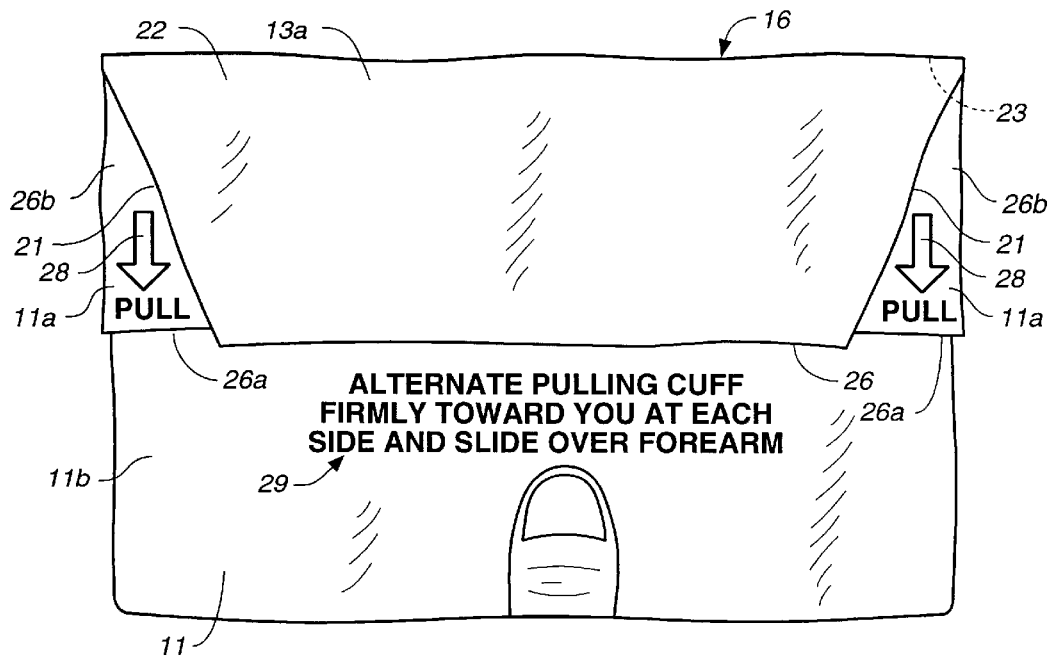
FIG._9
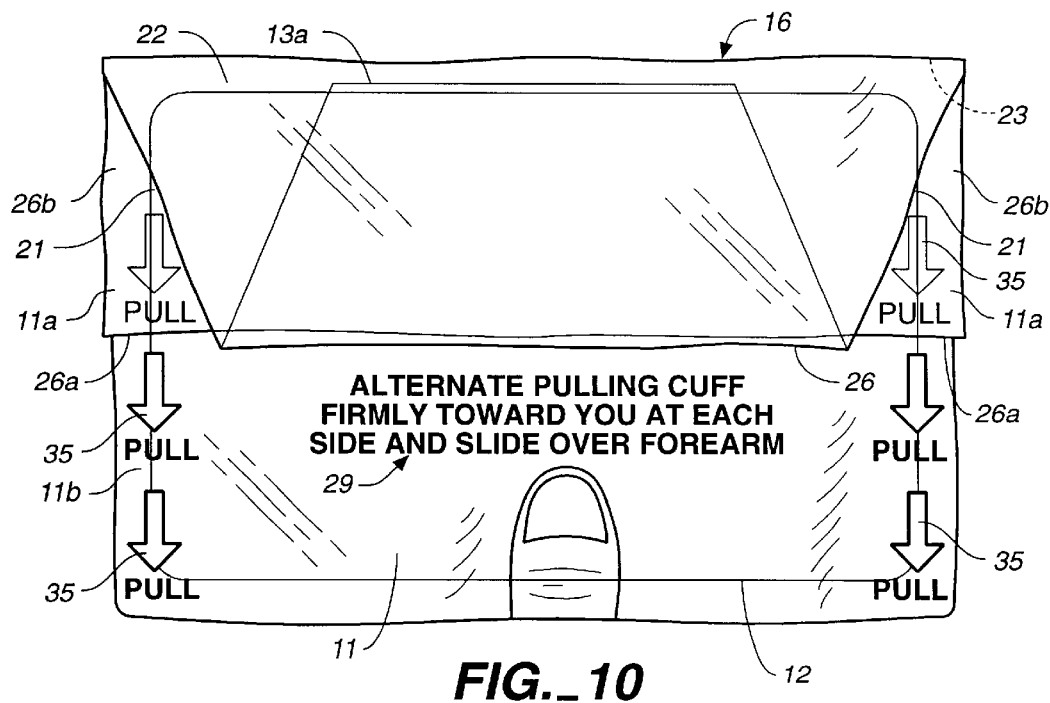
FIG._10

METHOD AND PACKAGING SYSTEM FOR PACKAGING A STERILIZED ITEM

This is a continuation-in-part of 09/616,100 filed on Jul. 14, 2000 now U.S. Pat. No. 6,578,348.

BACKGROUND AND SUMMARY OF THE INVENTION

The present invention relates to a packaging system, a method for packaging a sterilizable item for aseptic presentation onto a sterile field, and a packaging element having instructional information printed thereon.

In U.S. Pat. No. 5,638,661, I teach a method and packaging system for packaging a sterilizable item (including its container) in which a sterilizable item is placed into a flexible elongate tubular member (pouch), which tubular member is sized relative to the item being wrapped. After the tubular member is folded and secured as taught, the sterilizable item is sterilized. The packaging system can be opened and the item dispensed onto a sterile field in a manner that prevents the inadvertent contamination of the sterilized item.

The method and packaging system for packaging a sterilizable item of U.S. Pat. No. 5,638,661 requires that the vertical orientation of the sterilizable item be reversed (turned over) as part of the packaging and unpackaging process. For many sterilizable items, this does not pose any problem, but for some sterilizable items, it is required that the vertical orientation not be reversed during or between packaging and unpackaging. That is, the item has an "up" side that must be maintained "up" at all times prior to use.

Accordingly, it is an object of the present invention to provide a method and packaging system for packaging a sterilizable item (including its container, if it has one) wherein the sterilizable item can be packaged, sterilized and unpackaged without inverting its orientation (turning it over). In achieving this objective, the present invention continues to possess all of the advantages of the invention disclosed in prior U.S. Pat. No. 5,638,661.

Another object of the present invention is to provide a packaging element as specified above which has information printed thereon which is exposed after the packaging element is used according to the inventive packaging system and method.

The foregoing and other objectives, features and advantages of the invention will be more readily understood upon consideration of the following detailed description of the invention taken in conjunction with the accompanying drawings.

BRIEF DESCRIPTION OF THE DRAWINGS

FIG. 1 is a representation of an exemplary packaging system for a sterilizable item embodying the present invention.

FIG. 2 is a representation of an inner packaging element for the packaging system shown in FIG. 1 in the initial stage of unpackaging.

FIG. 3 is an illustration of the inner packaging element prior to folding;

FIG. 4 is an illustration of the inner packaging element partially folded and in relation to the item to be sterilized;

FIG. 5 is an illustration of the inner packaging element in an intermediate stage of folding;

FIG. 6 is an illustration of the inner packaging element in an intermediate stage of folding;

FIG. 6A is an illustration of an alternative embodiment of the packaging element shown in an intermediate stage of folding;

FIG. 7 is an illustration of the inner packaging fully folded;

FIG. 7A is an illustration of an alternative embodiment of the packaging element shown fully folded;

FIG. 8 is a representation illustrating the aseptic presentation of the item shown in FIG. 2.

FIG. 9 is a representation illustrating information printed on the packaging element for the packaging system shown in FIG. 1.

FIG. 10 is essentially the same as FIG. 9, except that the illustrated packaging element is made of transparent polyethylene material.

DETAILED DESCRIPTION OF THE PREFERRED EMBODIMENTS

Referring now to an exemplary first embodiment illustrated in FIGS. 1–7, a packaging system 10 (FIG. 1) for a sterilizable item 12 includes an outer packaging element 14 surrounding an inner packaging element 16.

Referring to FIG. 3, the inner packaging element 16 is a sterilizable flexible pouch having a closed end 18 and an open end 19 and, in a preferred embodiment, is made by attaching a front panel 11 having an inside surface 11a and an outside surface 11b to a back panel 13 having an inside surface 13a and an outside surface 13b with at least one side seam and a bottom seam. Thus, the pouch 16 has a closed end 18, an open end 19, inside surfaces 11a and 13a, and outside surfaces 11b and 13b. The pouch 16 may be made from a reusable fabric, such as a woven fabric, or from a disposable, single-use material, such as a non-woven fabric or a polymeric film.

Thus, the packaging element 16 of the invention is formed by a front panel 11 having an inside surface 11a and an outside surface 11b, a back panel 13 having an inside surface 13a and an outside surface 13b attached to the front panel, with the inside surfaces of the front and back panels in facing relationship to form pouch 16 having a closed end 18, two sides and an open end 19 wherein the pouch is closed along at least one side.

Referring to FIGS. 3, 4 and 5, the item 12 is placed into the pouch 16 so that the item contacts a portion of inside surfaces 11a and 13a at or near the closed end 18. The pouch 16 is sized in proportion to the particular item 12 to be enclosed. In general, the circumference of the open end of the pouch is preferably about 10–15% larger than the circumference of the item as measured when the item is oriented so that the widest part 12a of the item 12 corresponds with the width 16a of the pouch 16. Typically, the length 16b of the pouch 16 is approximately 3.5 times the height 12b of item 12. For some items, however, that ratio will be different. In all cases, the length 16b of pouch 16 must be sufficient to enclose the hand, wrist and all or part of the forearm of a person unwrapping the item for presentation into a sterile field (FIG. 3).

Referring to FIG. 4, a border portion 22 (cuff) is formed on the pouch 16 so that a first edge 24 of the border portion defines an opening 20, which opening terminates in corners 20a and 20b. A second opposing edge 26 of border portion 22 terminates in corners 22a and 22b and is spaced apart from the first edge 24 by the length 30 of the border portion. The border portion 22 is preferably formed on the pouch 16 by folding over a circumferential cuff so that a first portion of the outside surfaces 11b and 13b of the pouch 16 contact a second portion of the outside surfaces 11b and 13b. A portion of the inside surfaces 11a and 13a of the pouch 16 are thus exposed and along the length 30 of the border portion 22.

Referring to FIG. 5, the width of the opening 20 in the pouch 16 is reduced by approximately 50 to 80% to the reduced edge 27 by folding the corners 20a and 20b inward along fold lines 21 onto the border portion 22. The length of reduced edge 27 is at least approximately 20% of second edge 26 (or of the original width 16a of opening 20) in order to achieve a secure lock when the reduced edge 27 is tucked under the second edge 26 (see FIG. 7). If the edge 27 is reduced to zero (e.g., edge 27 reduced to a point), a secure lock will not be formed by tucking edge 27 under second edge 26.

Referring to FIG. 6, an upper fold line 23 is formed in the border portion 22 above the item 12 separating border portion 22 into a folded-over portion 22c and an unfolded-over portion 22d. The reduced edge 27 of the border portion 22 is thereby located proximate the outside surface 11b of the front panel 11. The reduced edge 27 of the border portion 22 is folded along line 21a (FIG. 7) then placed under the second edge 26 of the border portion 22 between the border portion and the outside surface 11b of the front panel 11.

Referring to FIGS. 4 and 5, typically, the length 30 of the border portion 22 is sufficient both to locate the second unattached edge 26 proximate the middle third of the item 12 in the pouch 16, and to permit between one-third and one-fourth of the length 30 of the border portion 22 to be tucked under the second edge 26 (FIG. 7). The size and shape of item 12 to be wrapped by packaging element 16 dictate where, along the length of the element 16, the unattached edge 26 is located. In some cases, it will be in the upper or lower third of the item 12. The fraction of the border portion 22 that is tucked under the unattached edge 26 can also vary from the typical one-third to one-fourth ratio.

Referring to FIGS. 1 and 2, when the reduced edge 27 of the border portion 22 has been secured under the second edge 26 and onto the front panel 11 of the pouch 16, portions 26a of the second edge 26 proximate the corners 22a and 22b remain accessible for grasping without turning over the item 12. Tape 25 may be applied to receive the border portion 22 to the front panel 11, if desired, to form a tamper-proof seal. The item 12 in the sealed pouch 16 may be sterilized without additional packaging.

In addition to achieving a secure lock by tucking the reduced edge 27 of the folded border portion 22 under the second edge 26 of the border portion 22 between the border portion 22 and the outside surface 11b of the pouch 16, the folds along lines 21 and 21a (FIG. 7) create a barrier that seals the opening 27 against exterior contamination.

Referring to FIG. 7A, the folded-over portion 22c of border portion 22 can be folded onto itself along lower fold line 21a (without tucking under edge 26) so that the reduced edge 27 is between the upper fold line 23 and lower fold line 21a and between the folded-over border portion 22c and the unfolded-over border portion 22d. This folding procedure also seals opening 27.

In an alternative embodiment of the invention (FIGS. 6A and 7A), the folded-over portion 22c of border portion 22 is not tucked under the edge 26, but rather folded onto itself along lower fold line 21a as described above and taped down onto outside surface 11b of front panel 11 by tape 25. In order to unwrap the package, the tape is released and the same procedure followed as with the tucked-under embodiment.

Referring to FIG. 1, the packaging system 10 is completed by placing the inner packaging element—pouch 16—which encloses the item 12, into the outer packaging element 14. The outer packaging element 14 is a sterilizable container, such as a sealable two-piece, peel-apart pouch, or a CSR cover. The packaging system 10 is sterilized by any convenient method suitable for the item and the materials used in the packaging system. After sterilization, as long as the outer packaging element 14 remains unopened and undamaged, the inner packaging element—pouch 16—and the item 12 remain sterile and ready to use.

The packaging system 10 is readily opened for aseptic presentation of the sterile item 12. The non-scrubbed attendant opens the outer packaging element 14, for example, by peeling apart the two sections of the sealed pouch (FIG. 1) and unpackaging the inner packaging element—pouch 16— (FIG. 2). Referring to FIGS. 2 and 8, the attendant holds the inner packaging element 16 in one hand 32 at the closed end 18 with its front panel 11 and the portion 26a of the edge 26 facing the attendant and accessible for grasping. With a second hand 34, the attendant grasps one of the edge portions 26a of the border 20 portion 22 at one side of the item 12. The attendant pulls on the edge portion 26a of the border portion 22 at alternate sides of the item 12 until the first edge 24 of the border portion 22 is released from under the second edge 26. In the alternative embodiment (FIGS. 6a and 7a), the tape 25 is simply released. The attendant continues to pull on the edge portion 26a until the pouch 16 has been turned inside out to expose generally the entire inside surfaces 11a and 13a, while, in the process, covering the attendant's hand 32 and forearm 32a with the outside surfaces 11b and 13b of the pouch 16 (FIG. 3). With hand 32 and forearm 32a thus covered and protected, the non-scrubbed attendant may aseptically place the item 12 directly onto the sterile surgical field, eliminating the need for a scrubbed assistant.

At no step in the process of packaging, sterilizing, unpackaging or presenting the sterilized item into the sterile field is it necessary to invert the item being sterilized.

Importantly, the possibility of inadvertent contamination of the item and the sterile field is eliminated. Thus, one would expect a reduction in the incidence of post-operative infection when using the packaging system of the present invention in the operating room and a concomitant reduction in cost.

Referring to FIG. 9, the folding process of the present invention for a pouch 16 of opaque material not only leaves exposed portions 26a of second edge 26 for grasping to initiate the unpackaging process, but also exposes portions of the inside surface 11a of front panel 11 at areas 26c proximate second edge 26 at corners 22a and 22b and above edge portions 26a. Areas 26b being exposed (visible) when the item 12 to be sterilized is in its required vertical orientation ("up") provides the preferred location on which to print instructional information 28 in the form of words and/or symbols. Precisely where the edges 26a need to be grasped, instructions for doing so appear. Moreover, the package can be unwrapped while maintaining proper vertical orientation and achieves the other important benefits of the invention. In the prior art, it is necessary to turn the package over after completing the folding process to find the location and instructions for initiating the unwrapping process. Additional instructional information 29 (including the representation of a thumb where the users thumb should be placed) is printed on surface 11b near the bottom of panel 11.

"Printed" as used herein refers to any manner of creating visibly perceptible information on the inside or outside surfaces of front panel 11 or back panel 13.

Instructional information 28 relating to use of the invention is advantageously printed on the inside surface 11a of the front panel 11 after the border portion 22 is formed.

Referring to FIG. 10, a pouch 16 is formed of a clear material, such as polyethylene, which is most advantageously manufactured by a process that does not readily permit the border portion 22 to be formed prior to printing. Thus, printed "PULL" instructions 35 and instructional information 29 appear on the outside pouch surface 11b only. Because the pouch is made of transparent material, the "PULL" instructions 35 adjacent the edges 26 that underlay the border portion 22 can be seen. By printing the "PULL" instructions 35 all along the edges of panel 11 on surface 11b, there will be a "PULL" instruction adjacent each pull edge 26a, regardless of the location of the unattached edge 26 on panel 11. As with the opaque woven material, the instructional information 29 (including thumb locator) is printed near the bottom of panel 11 on surface 11b.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. A method for packaging a sterilizable item for aseptic presentation, comprising:
   (a) into a sterilizable pouch having a closed end, an open end, an inside surface and an outside surface, place the item to be sterilized so that the item contacts a portion of the inside surface proximate the closed end;
   (b) form a border portion which surrounds and overlays the outside surface of the pouch, a first edge of said border portion defining an opening in said pouch which terminates m spaced-apart first edge corners and a second opposing edge of the border portion being spaced apart from the first edge by a length of the border portion;
   (c) reduce the size of the first edge by between approximately 50 to 80% by folding the corners inward onto the border portion;
   (d) fold the border portion over the corners along an upper fold line between the first edge and the second edge so that the reduced open end extends toward the second edge and the upper fold line separates a folded-over portion of the border portion from an unfolded-over portion of the border portion; and
   (e) fold the folded-over border portion onto itself along a lower fold line so the reduced first edge is positioned between the lower fold line and the upper fold line without tracking any portion of the folded-over portion under the second edge.

2. The method of claim one including the further step of: securing the folded border portion to the outside surface of the pouch.

3. The method of claim 1 wherein in step (d), at least a portion of said inside surface of a first panel of said pouch is in contact with at least a portion of said inside surface of a second panel of said pouch.

4. The method of claim 1 wherein said border portion is formed by folding over a circumferential cuff so that a first portion of an outside surface of said pouch is in contact with a second portion of said outside surface of said pouch, and a portion of an inside surface of said pouch defines said length of said border portion.

5. The method of claim 1 wherein said second edge of said border portion is located proximate the middle third of the item in said pouch.

6. The method of claim 1, including the step of placing said pouch into a second packaging element.

7. The method of claim 1, including the step of sterilizing said item.

8. A package according to the method of claim 7.

9. The package according to the method of claim 1.

10. A packaging element for containing an item to be sterilized, comprising in combination:
    a front panel having an inside surface and an outside surface;
    a back panel having an inside surface and an outside surface attached to said front panel, with the inside surfaces of said front and back panels in facing relationship to form a pouch having a bottom, two sides and a top wherein said pouch is closed along its bottom and at least one side and open at its top;
    instructional information printed onto the inside surface of said front panel at locations thereon which are exposed when said pouch is folded as follows:
    (a) form a border portion which surrounds and overlays the outside surfaces of said front and back panels, a first edge of said border portion defining an opening in said pouch and having a width between two spaced-apart first edge corners and a second opposing edge of the border portion having a width between two second edge corners and being spaced apart from the first edge by the length of the border portion;
    (b) reduce the size of the first edge by between approximately 50 to 80% by folding the first edge corners inward onto the border portion;
    (c) fold the border portion over the first edge corners along an upper fold line between said first edge of said border portion and said second edge of said border portion so that the reduced first edge extends toward the second edge whereby the upper fold line separates a folded-over portion of the border portion from an unfolded-over portion of the border portion; and
    (d) fold the folded-over border portion onto itself along a lower fold line so the reduced first edge is positioned between the lower fold line and the upper fold line and between the folded-over portion of the border portion and the unfolded-over portion of the border portion without tucking any portion of the folded-over portion under the second edge.

11. The packaging element of claim 10 further including tape securing the folded-over border portion to the outside surface of the pouch.

12. The packaging element of claim 11 wherein said pouch is closed on both sides.

13. The packaging element of claim 11 wherein instructional information is printed proximate the corners of the second edge of the border portion.

14. The packaging element of claim 13 wherein additional instructional information is printed on the outside surface of said front panel adjacent the bottom of said pouch.

15. The packaging element of claim 14 wherein the instructional information printed on the inside surface of said back panel appears between the location where the border portion and pouch-forming front and back panels are folded over the corners toward said front panel and the second edge of the border portion.

16. A packaging element for containing an item to be sterilized, comprising in combination;
    a front panel of transparent material having an inside surface and an outside surface;

a back panel of transparent material having an inside surface and an outside surface attached to said front panel with the inside surfaces of said front and back panels in facing relationship to form a pouch having a bottom, two sides and a top wherein said pouch is closed along its bottom and at least one side and open at its top;

instructional information printed onto the outside surface of said front panel along the sides of said pouch which is exposed when said pouch is folded as follows:
  (a) form a border portion which surrounds and overlays the outside surfaces of said front and back panels, a first edge of said border portion defining an opening in said pouch and having a width between two spaced-apart first edge corners and a second opposing edge of the border portion having a width between two second edge corners and being spaced apart from the first edge by a length of the border portion;
  (b) reduce the size of the first edge by between approximately 50 to 80% by folding the first edge corners inward onto the border portion;
  (c) fold the border portion and pouch-forming front and back panels over the corners toward said front panel so that the reduced first edge extends beyond the second edge; and
  (d) fold the folded border portion onto itself along a lower fold line so the reduced first edge is positioned between the lower fold line and the upper fold line so that no part of the folded border portion is tucked under the second edge of the border portion, whereby the instructional information appears adjacent the exposed portions of the second opposing edge of the border portion and under said areas of said border portion immediately above said exposed second opposing edge portions.

17. The packaging element of claim 16 wherein printed instructional information appears near the bottom of said front panel of said pouch.

18. The packaging element of claim 16 further comprising the step of:
  (e) securing the folded-over portion with tape.

19. A packaging element for containing an item to be sterilized, comprising in combination:
  a front panel having an inside surface and an outside surface;
  a back panel having an inside surface and an outside surface attached to said front panel, with the inside surfaces of said front and back panels in facing relationship to form a pouch having a bottom, two sides and a top wherein said pouch is closed along its bottom and at least one side and open at its top;

instructional information printed onto the inside surface of said front panel at locations thereon which are exposed when said pouch is folded as follows:
  (a) form a border portion which surrounds and overlays the outside surfaces of said front and back panels, a first edge of said border portion defining an opening in said pouch and having a width between two spaced-apart first edge corners and a second opposing edge of the border portion having a width between two second edge corners and being spaced apart from the first edge by a width of the border portion;
  (b) reduce the size of the first edge by between approximately 50 to 80 percent by folding the corners inward onto the border portion; and
  (c) fold the border portion and pouch-forming front and back panels over the corners onto said front panel, and;
  (d) secure said folded-over border portion and pouch-forming front and back panels in their folded-over position.

20. The packaging element of claim 19 where the folded-over portion is secured by tape.

* * * * *

UNITED STATES PATENT AND TRADEMARK OFFICE
CERTIFICATE OF CORRECTION

PATENT NO. : 6,672,036 B2  Page 1 of 1
DATED : January 6, 2004
INVENTOR(S) : Percival C. Banks It is certified that error appears in the above-identified patent and that said Letters Patent is hereby corrected as shown below:

<u>Column 5,</u>
Line 50, should read -- ...without trucking any portion of the folded-over portion.... --

Signed and Sealed this

Eighteenth Day of May, 2004

JON W. DUDAS
*Acting Director of the United States Patent and Trademark Office*